US007026488B2

(12) United States Patent
Maeda et al.

(10) Patent No.: US 7,026,488 B2
(45) Date of Patent: Apr. 11, 2006

(54) ANTITUMOR AGENTS AND PROCESS FOR PRODUCING THE SAME

(75) Inventors: Hiroshi Maeda, 21-24 Koto 3-chome, Kumamoto-shi, Kumamoto (JP) 862-0909; Tomohiro Sawa, Kumamoto (JP)

(73) Assignee: Hiroshi Maeda, Kumamoto (JP)

( * ) Notice: Subject to any disclaimer, the term of this patent is extended or adjusted under 35 U.S.C. 154(b) by 0 days.

(21) Appl. No.: 10/484,726

(22) PCT Filed: Aug. 29, 2002

(86) PCT No.: PCT/JP02/08707

§ 371 (c)(1),
(2), (4) Date: Feb. 17, 2004

(87) PCT Pub. No.: WO03/018007

PCT Pub. Date: Mar. 6, 2003

(65) Prior Publication Data

US 2004/0234495 A1    Nov. 25, 2004

(30) Foreign Application Priority Data

Aug. 31, 2001    (JP)    ............... 2001-264918

(51) Int. Cl.
 *C07D 209/56*    (2006.01)
 *C07D 53/00*    (2006.01)
(52) U.S. Cl. ........................ 548/402; 525/88
(58) Field of Classification Search ............... 540/145; 424/9.362; 514/185, 410
See application file for complete search history.

(56) References Cited

U.S. PATENT DOCUMENTS

| | | | | |
|---|---|---|---|---|
| 5,601,802 A | * | 2/1997 | Hemmi et al. | ........... 424/9.363 |
| 5,622,685 A | * | 4/1997 | Sinn et al. | .................. 424/1.65 |
| 5,849,259 A | | 12/1998 | Hilger et al. | |
| 6,362,175 B1 | * | 3/2002 | Vinogradov et al. | ........ 514/185 |
| 2002/0155999 A1 | * | 10/2002 | Han | .............................. 514/8 |

FOREIGN PATENT DOCUMENTS

| | | | |
|---|---|---|---|
| EP | 538228 A1 | * | 4/1993 |
| GB | 2360785 A | * | 10/2001 |
| WO | 91/18006 A | | 11/1991 |
| WO | WO 9529915 A1 | * | 11/1995 |

OTHER PUBLICATIONS

Sahoo, S.K., et al., "Pegylated Zinc Protoporphyrin: A Water-Soluble Heme Oxygenase Inhibitor with Tumor Targeting Capacity," Bioconjugate Chemistry, vol. 13, pp. 1031-1038 (available on the World Wide Web Jul. 16, 2002).*

Iida, K., et al., "Energy Transfer and Electron Transfer of Poly(ethylene glycol)-Linked Fluorinated Porphyrin Derivatives in Lipid Bilayers," Langmuir, vol. 12, pp. 450-458 (1996).*

Doi, K., "Induction of haem oxygenase-1 by nitric oxide and ischaemia in experimental solid tumours and implications for tumour growth," Brit. J. Cancer, vol. 80(12), pp. 1945-1954 (1999).*

Maines, M., "Heme oxygenase: function, multiplicity, regulatory mechanisms, and clinical applications," FASEB J., vol. 2(10) pp. 2557-2568 (1988) at p. 2557, col. 2, lines 2-6 and 39-42.*

Maines, M., "Zinc-protoporphyrin is a selective inhibitor of heme oxygenase activity in the neonatal rat," Biochimica et Biophysica Acta, vol. 673, vol. 673, pp. 339-350 (1981), in Abstract, lines 9-11.*

(Continued)

*Primary Examiner*—Kamal A. Saeed
*Assistant Examiner*—Andrew B. Freistein
(74) *Attorney, Agent, or Firm*—Nixon & Vanderhye P.C.

(57) ABSTRACT

Anticancer agents which contain as the active ingredient, a heme oxygenase inhibitory metalloporphyrin derivatives which are conjugated with amphipathic or water-soluble polymers (in particular, Zn-protoporphyrin (ZnPP) conjugated with polyethylene glycol). Because of being conjugated to amphipathic or water-soluble polymers, such as polyethylene glycol, the active ingredient can be administered by intravenous injection and can exert a remarkable anticancer effect owing to tumor selective delivery.

1 Claim, 5 Drawing Sheets

OTHER PUBLICATIONS

Woehrle, D., et al., "Polymer-bound porphyrins and their precursors. 10. Syntheses and photoredox properties of water-soluble polymers with covalently bonded zinc tetraphenyl-porphyrin," Die Makromolekulare Chemie, vol. 192, pp. 819-832 (1991).*

Abòs, P. et al., "Polymer bound pyrrole compounds, IX . . . .mesoporphyrin IX covalently bound to a low molecular weight polyethylene glycol," Journal of Photochemistry and Photobiology, vol. 41, pp. 53-58 (1997) at p. 53, col. 2, lines 4-12.*

Awanda, A., "The pipeline of new anticancer agents for breast cancer treatment in 2003," Critical Reviews in Oncology/Hematology, vol. 48, pp. 45-63 at p. 46, 2nd col., line 3.*

Doi et al.; "Induction of Heme Oxygenase-1 by Nitric Oxide and Ischaemia in Experimental Solid Tumors and Implications for Tumor Growth"; Br. J. Cancer, 1999, vol. 80, No. 12, pp. 1945 to 1954.

Sahoo et al; "Pegylated Zinc Protoporphyrin: A Water-Soluble Heme Oxygenase Inhibitor with Tumor", Targeting Capacity, Bioconjugate Chem., 2002, vol. 13, No. 5, pp. 1031 to 1038.

Journal of Chinese Pharmaceutics, vol. 30, No. 12 (1995), pp. 746-478 w/English Abstract.

* cited by examiner

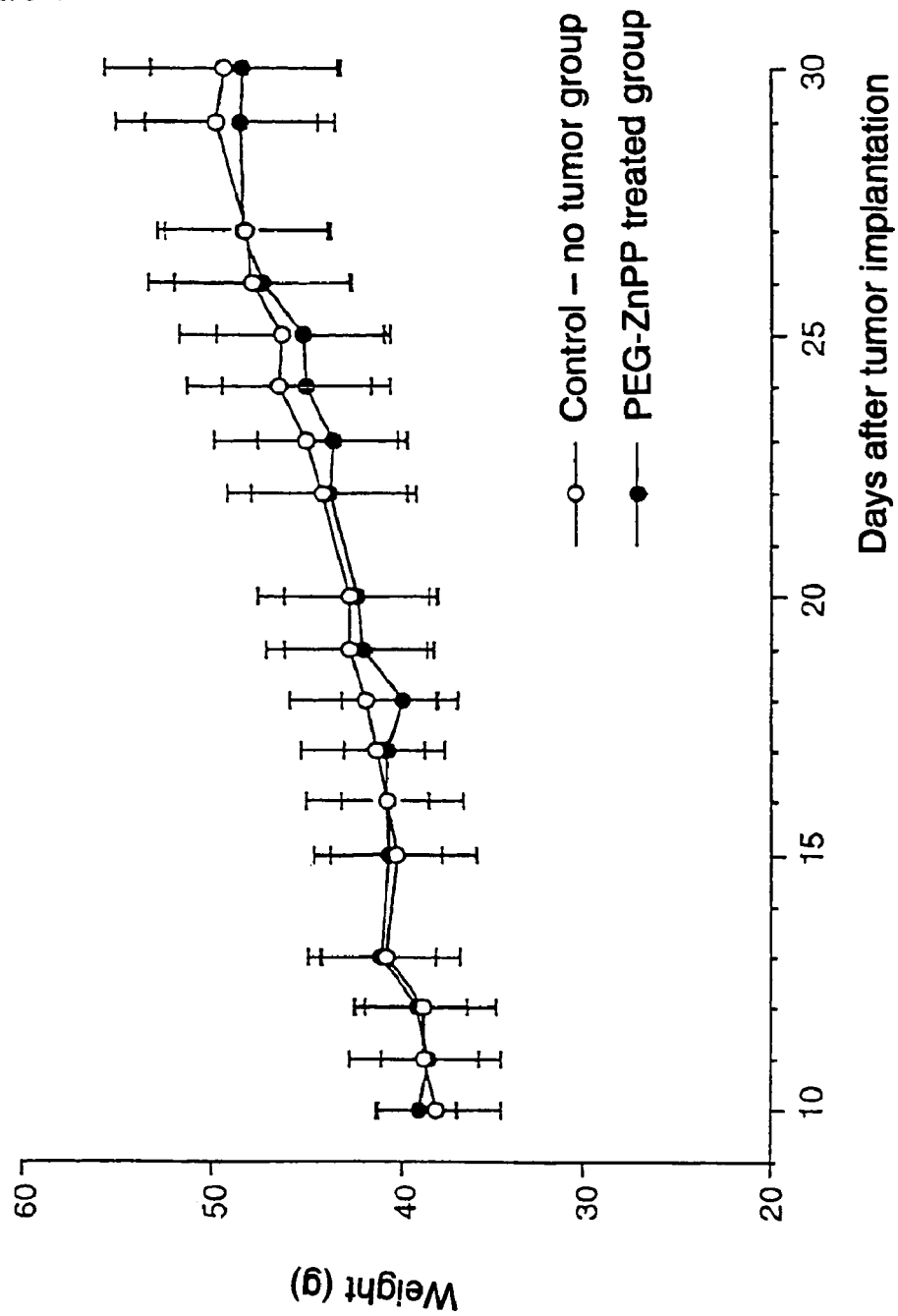

ANTITUMOR AGENTS AND PROCESS FOR PRODUCING THE SAME

This application is the US national phase of international application PCT/JP02/08707 filed Aug. 29, 2002, which designated the US. PCT/JP02/08707 claims priority to JP Application No. 2001-264918 filed 31 Aug. 2001. The entire contents of these applications are incorporated herein by reference.

FIELD OF THE INVENTION

The present invention relates to anticancer agents with little side effect and excellent tumor accumulation thereby exhibiting very potent anticancer effect, and the preparation method of the same. More precisely, it relates to anticancer agents containing as the active ingredient heme oxygenase inhibitory metalloporphyrin derivatives that are conjugated with amphipathic or water-soluble polymers. And it relates to also a preparation method of the same with high efficiency.

BACKGROUND TECHNOLOGY

The inventors of the present invention have investigated relationship between cancer growth or its suppression and activity of heme oxygenase, and found that heme oxygenase is highly expressed in tumor tissues. The heme oxygenase degrades heme and produces bilverdin, carbon monoxide and free iron in tumor or normal tissues.

Bilverdin is readily converted into bilirubin in the cells, and this bilirubin is a very potent antioxidant. Thereby, bilirubin can be a defense molecule against active oxygen such as superoxide, $H_2O_2$, or nitric oxide etc that are generated by leukocytes of the hosts (cancer patients). Namely, bilirubin, thus generated will nullify the toxic oxidative defense power against cancer cells or infecting microbes of the host. Therefore, if one blocks heme oxygenase, no bilirubin will be available and tumor cells will be killed by the oxidative molecules generated by leukocytes as a result of innate defense state.

The inventors had tried to see the antitumor effect of zinc protoporphyrin (ZnPP), an inhibitor of heme oxygenase, administered into the tumor feeding artery of tumor bearing rats thereby targeting the inhibitor into the tumor loci selectively, and they indeed confirmed antitumor effect in rats (K. Doi et al.: Br. J. Cancer 80, 1945–54, 1999).

However, there are several problems to use ZnPP per se as an antitumor agent. First, it is almost insoluble in water per se, thus, we had to use oily formulation to solubilize ZnPP, and such oily formulated agent may be only injectable via the tumor-feeding artery, and this is rather too elaborate and far advanced skill is required for this procedure compared with ordinary intravenous or subcutaneous injection. Second, native or original ZnPP has no guarantee for selective accumulation of ZnPP in cancer tissues, and to exert tumor selective anticancer effect, whereas the drug will be widely distributed to whole body besides tumor. Therefore, unexpected side effects are concerned.

On the contrary, the inventors are experts in tumor biology, particularly study on the vascular permeability of solid tumor tissues, and knowledgeable that macromolecular therapeutics would permeate more selectively at the tumor tissue by virtue of unique anatomical character and by the effect of multiple vascular permeability factors; and further, those macromolecules are retained in the tumor tissues for long period. Thus, this phenomenon was coined "enhanced permeability and retention (EPR)-effect" (Y. Matsumura, H. Maeda: Cancer Res. 47: 6387–92, 1986; H. Maeda: In Advances in Enzyme Regulation (by G. Weber ed), Elsevier Scientific Ltd., Amsterdam, 41, 189–207, 2001).

According to the EPR-effect, drugs with molecular size larger than 40,000 exhibit high concentration in blood plasma for prolonged time, and several hours to days after intravenous injection; whereas intratumoral concentration will result in several fold higher more precisely in 24–48 hr time. This means, making the apparent drug size greater than 40,000, would make it possible for selective tumor targeting of such macromolecular drugs.

Meantime, various metal porphyrin derivatives having inhibitory activity against heme oxygenase, and improved method of their administrations as a whole were studied. The resulted finding is that amphipathic or water soluble polymer conjugation to the metal protporphyrins made it possible to yield water soluble metal porphyrin derivatives and they can be administered not only arterially but also intravenously which has more versatile and easy clinical usage. They exhibited EPR-effect by polymer conjugation yielding highly efficient accumulation in tumor, and enzyme inhibitory activity against heme oxygenase is retained for long period. As a result, only 2 to 3 times of injections made it possible to suppress tumor growth completely in mice, which was a remarkable result.

Previously, metal porphyrin derivatives possessing heme oxygenase inhibitory activity with amphipathic or water soluble polymer conjugation were never reported, nor were the method of their preparation before our own. Present inventors have developed the method for synthesis of amphipathic or water-soluble polymer conjugation of metalloporphyrin via amide linkage. Resultant polymer conjugated metalloporphyrin derivatives are novel series of compounds not reported previously.

DISCLOSURE OF THE INVENTION

The present invention is anticancer agents containing as the active ingredient a metalloporphyrin derivatives having inhibitory activity against heme oxygenase, especially Zn-protoporphyrin (ZnPP) conjugated with amphipathic polymers which are both water and lipid soluble or water soluble polymers.

The present invention is also a series of novel useful compounds for an ingredient of anticancer agents where amphipathic or water-soluble polymers and heme oxygenase inhibitory metalloporphyrin derivatives are conjugated via amide bonds, and preparation method of the compounds.

BRIEF EXPLANATIONS OF DRAWINGS

FIG. 5 shows the profile of body weight change during or after intravenous administration of PEG-ZnPP.

MOST PREFERABLE EMBODIMENT FOR CARRYING OUT THE INVENTION

Figure 1:
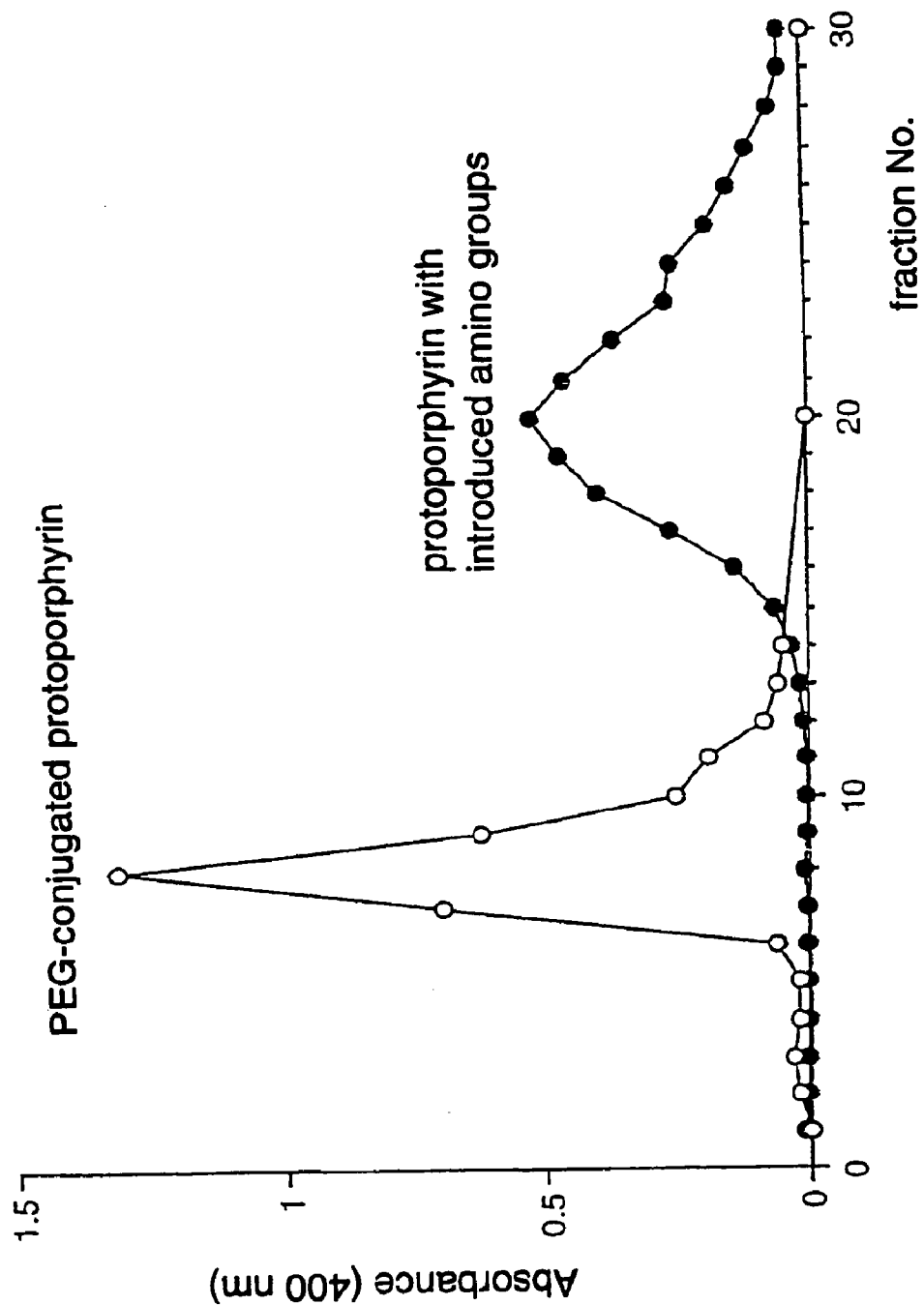
FIG. 1 shows the gel filtration chromatography of diaminoethane coupled protoporphyrin and PEG-conjugated protoporphyrin.

Amphipathic or water soluble polymers to be conjugated include polyethylene glycol (PEG), poly propylene glycol (PPG), polyvinyl pyrrolidone (PVP), polyvinyl alcohol (PVA), various gelatins, and their derivatives such as succinylated form, polyamino acids (eg. polymerized aspartic acid, glutamic acid, lysine, alanine, glycine, proline, tyrosine, etc.), hydroxypropyl and other alkyl acrylate polymer, styrene-maleic acid copolymer (SMA), and their derivatives. Among these polymers with amphipathic and water-soluble characters, PEG and SMA are more preferable. PEG with molecular weight of 2000–5000 is preferably used.

SMA is copolymer of styrene and maleic acid in the alternative order where carboxyl group of maleic acid can be utilized to conjugate with metalloporphyrin directly or indirectly. SMA can be per se or its derivatives where maleic acid is partially esterified.

Metal porphyrin derivative is a complex porphyrin compound, where metal is chelated in stable coordination to the porphyrin ring, and protoporphyrin is preferably used because of its easy availability among porphyrin compounds.

Among the metals to be coordinated, iron that give no heme oxygenase inhibitory action, mercury with poisonous nature, monovalent metals which do not form coordinated chelation, can not be used. Although, various metals other than above such as zinc, tin, cobalt, and cupper can be used. Among them, tin and zinc complex are more preferred. However, tin is also known to be poisonous. Thus, ZnPP is the most preferable and its chemical structure of ZnPP is shown in Figure (B).

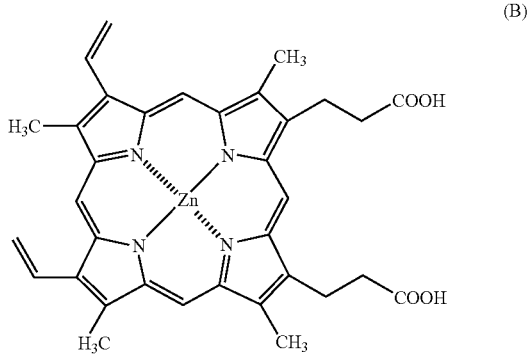

(B)

The anticancer agents of the present invention are any macromolecular compounds obtained by conjugation of metal porphyrin with amphipathic or water-soluble polymers. However we found it difficult to carry out the conjugation of the polymers to the metal porphyrin directly, because metal porphyrin derivative is water-insoluble. To undertake this chemical conjugation, it is preferable to conjugate the polymers to porphyrin before the coordination of metal, then to coordinate the metal.

The conjugation of porphyrin with the polymer can be facilitated directly as well as by introducing desired functional spacer group.

For example, in the case of synthesis of ZnPP, polymer can be directly conjugated to the two carboxyl groups in protoporphyrin, but this direct conjugation method is not advantageous because of poor activity of said carboxyl groups for this reaction. The inventors of the present invention studied effective synthesis methods of PEG conjugated ZnPP, and succeeded to synthesize ZnPP conjugated with PEG via amide bond (formula (A)).

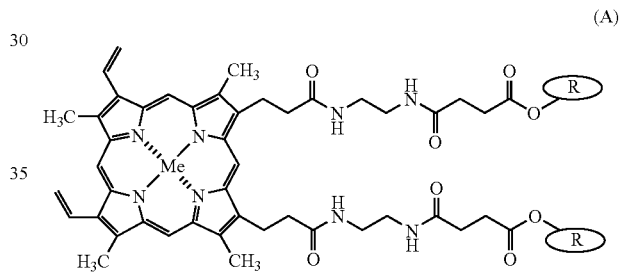

(A)

(Where R in above formula means amphipathic or water-soluble polymer, and Me is a metal.)

The polymer conjugated ZnPP (B) may be synthesized by successive reaction as follows:

(1) Introduction of amino group to protoporphyrin IX;
(2) Conjugation of the polymer, and lastly
(3) Coordination of Zn into porphyrin ring.

For example, the scheme of synthesis of PEG conjugated ZnPP is shown diagrametrically by stepwise reaction as follows.

[Reaction (a)] Protoporphyrin IX (compd.(1)) is activated with ethyl chloroformate in tetrahydrofuran (compd.(2)).

[Reaction (b)] Protoporphyrin with diamino group (compd.(3)) can be obtained by addition of ethylene diamine.

[Reaction (c)] PEG is introduced into protoporphyrin ring by addition of activated PEG (compd.4).

[Reaction (d)]. Lastly, PEG-ZnPP (compd.5) is obtained by addition of zinc acetate into the reaction product of the Reaction (d). One can replace Zn for tin (Sn) and obtain PEG-Sn-PP by addition of tin acetate

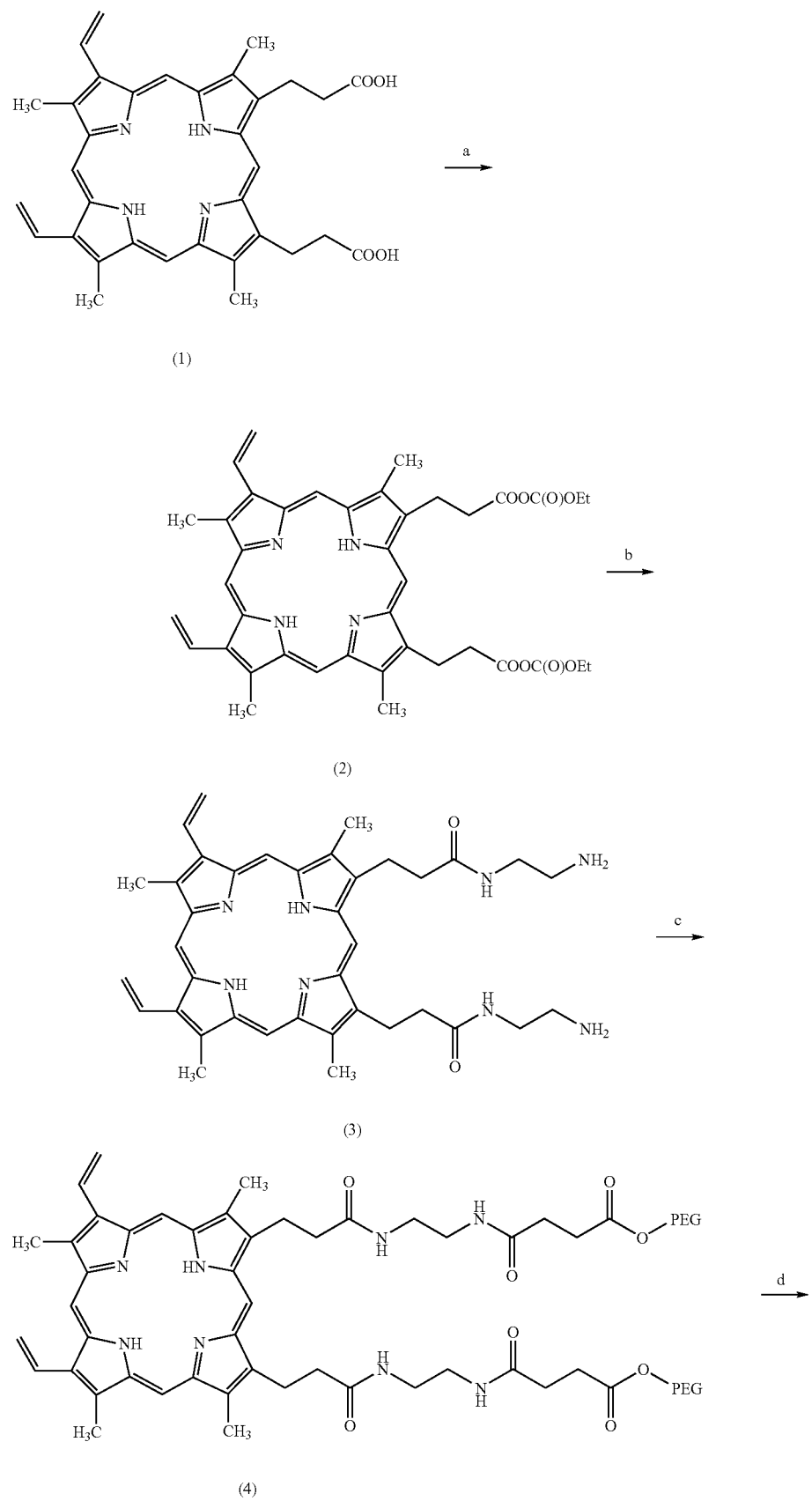

-continued

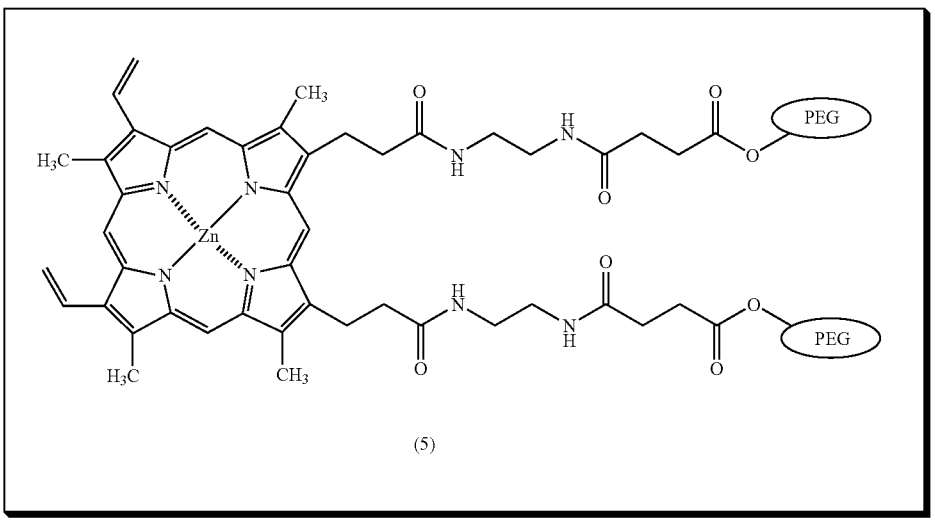

(5)

Other than PEG, with amphipathic or water soluble polymers, such as SMA can be attached to protoporphyrin similarly by condensation reaction of compd.(3) and SMA.

Heme oxygenase inhibitory methalloprotoporphyrin, that is conjugated with amphipathic or water-soluble polymers shown in formula (A) is selectively accumulated in solid tumor and exhibit excellent antitumor activity. Thus it is a novel and useful antitumor substance. The compd.(5), which is a typical example of the compound(A), wherein metal is zinc, and R is PEG, was synthesized by the scheme shown (a) to (d). The chemical structure of the reaction product was confirmed by following analysis.

Firstly, the evidence of the amino group of ethylene diamine that was introduced into protoporphyrin (compd.3) is confirmed by (1) Infrared spectra with absorbance at 1641 cm−1, 1552 cm−1 showed new formation of the amide bond in the compound (structure of compd.3)

(2) Determination of molecular weight of the compound by mass spectroscopy (MS) showed 646, identical to the value calculated by formula based on the compd.3.

Then, PEG (mw about 5000) was coupled to amino group introduced into the protoporphyrin (compd.3), and zinc is chelated. The structure of thus obtained ZnPP was identified by determination of the molecular weight and absorption spectra (UV/Vis).

Determination of the molecular weight showed mass of near 11,000 Da by TOF/MS (time of flight-mass spectroscopy). And UV absorption showing max peak at 425, 543, and 583 indicating formula (5) is PEG-ZnPP.

The scheme of PEG-ZnPP synthesis using protoporphyrin IX as starting material via reaction steps [a]–[d] is a novel manufacturing method.

Thus obtained polymer conjugated metalloporphyrin is readily water-soluble and it may be used as injection solution either intravenously or arterially.

EXAMPLES

Process for preparing the PEG-ZnPP, inhibitory activity of the PEG-Znpp towards heme oxygenase and anticancer effect of PEG-ZnPP by intravenous injection according to the present invention shall be explained in detail with the following examples. However it should be understood, that the present invention shall not limited to these examples.

Example of Manufacturing

Synthesis of Polyethylene Glycol Conjugated ZnPP (PEG-ZnPP)

100 mg of protoporphyrin IX was dissolved in 20 ml of tetrahydrofuran, and 2.45 ml of triethylamine was added to this solution. This solution was kept at about 0° C. on ice, then 1.7 ml of ethyl chloroformate was added to this by dropwise under stirring, and allowed to react further for two hrs. Subsequently, triethylamine HCl salt being formed was removed by filtration, and 1.2 ml ethylene diamine was added, and reaction was continued at room temperature for 24 hrs. The reaction mixture was then subjected to vacuum evaporation to remove tetrahydrofuran, and solid material obtained was washed 7 times with 50ml of distilled water yielding 60 mg of porphyrin derivative having two amino groups per molecule (reaction a and b).

Five mg of compound (3) was dissolved in 25 ml of chloroform, and 800 mg of succinimidoester of polyethylene glycol (Shearwater; PEG, MW5000) was added to this solution, and reacted for 24 hrs under stirring at room temperature [reaction c].

PEG-conjugated protoporpyrin thus obtained was subjected to gel filtration chromatography on Sephadex LH60 using chloroform as eluent. The result of the gel filtration chromatography showed unreacted aminated compound (3) did not exist in the preparation of PEG-conjugated protoporpyrin at all. It showed all aminated protoporphyrin reacted with PEG to form polymeric form of protoporphyrin. Unmodified protoporphyrin, if any, was eluted at fraction No. 20, where elution volume was similar to aminated protoporphyrin.

40mg of zinc acetate was added to the PEG-PP solution and allowed for two hrs at room temperature yielding PEG-conjugated zinc protoporphyrin (PEG-Zn-PP) (reaction d).

Experimental Example 1

Inhibitory Activity of PEG-ZnPP Against Heme Oxidase.

This was examined using purified heme oxygenase fraction derived from rat spleen. It was assayed at 37° C. in the presence of hemin, the substrate of heme oxygenase, cofactor (NADPH, nicotine adenine dinucleotide), and cytosolic fraction containing bilirubin reductase, in which biliverdin formed by the oxygenase is converted to bilirubin.

Figure 2:
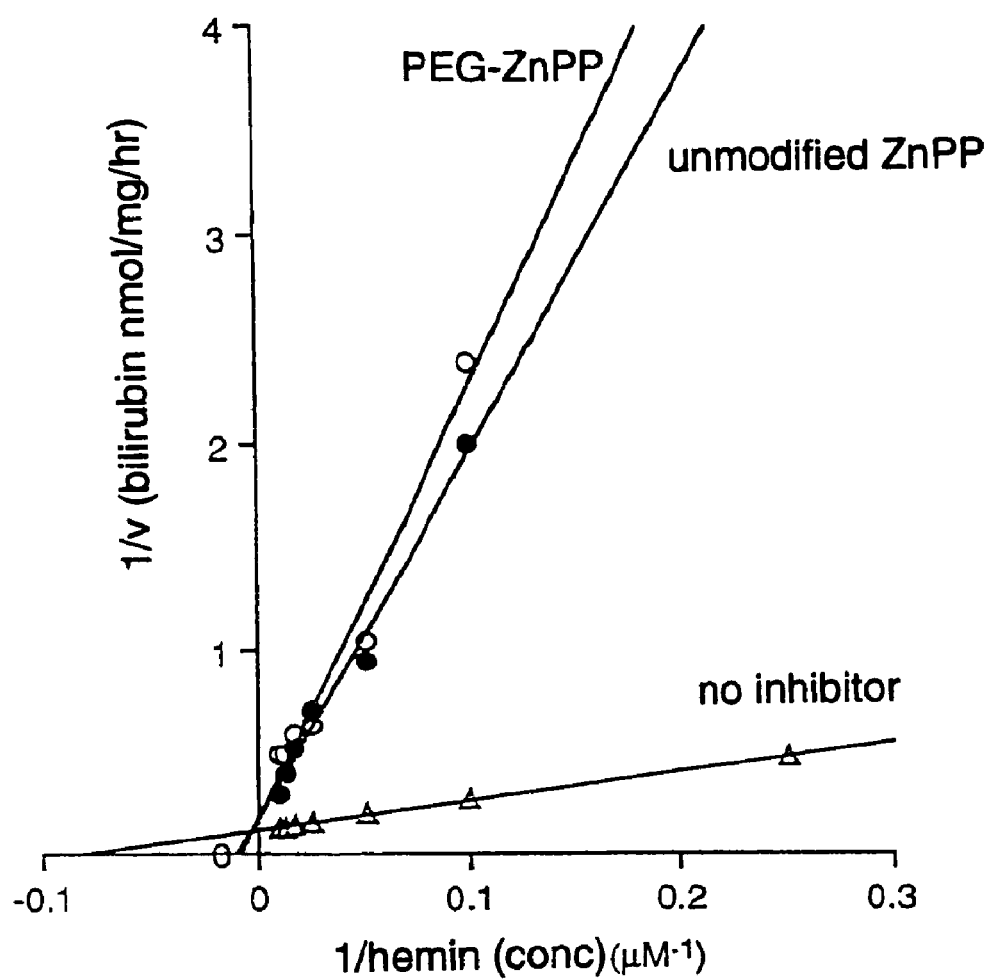
FIG. 2 shows Lineweaver-Burk plot of PEG-ZnPP inhibitory profile against heme oxygenase.

Bilirubin was extracted with chloroform and quantified by absorption at 465 nm. By the addition of either PEG-ZnPP, or unmodified ZnPP, or no inhibitor, their effect on heme oxidase was examined, and the Lineweaver-Burk plot of heme oxygenase activity was plotted during the inhibition by PEG-ZnPP. The result is shown in FIG. 2, indicating that PEG-ZnPP inhibits the heme oxygenase in a dose dependent manner, and inhibitory constant (Ki) was 0.13 μM. Mode of inhibition was competitive, and the value was equivalent to that of unmodified ZnPP. (Ki=0.12 μM)

Experimental Example 2

Effect of PEG-ZnPP on Cultured Tumor Cells.

Lung adenocarcinoma cell line A549 cells were plated in plastic dish and after overnight culture, 5 μM and 10 μM of PEG-ZnPP dissolved in distilled water were added to the culture dishes. Then, 8 hrs after cultivation at 37 ° C., a reagent that quantifies oxidative stress, called dichlorodihydrofluorescein diacetyl ester (DCDHF) was added and allowing cell culture for 30 minutes. Under oxidative stress, this DCDHF will be become oxidized and will fluoresce due to oxystress was generated by formation of fluorescein in cells.

Figure 3:
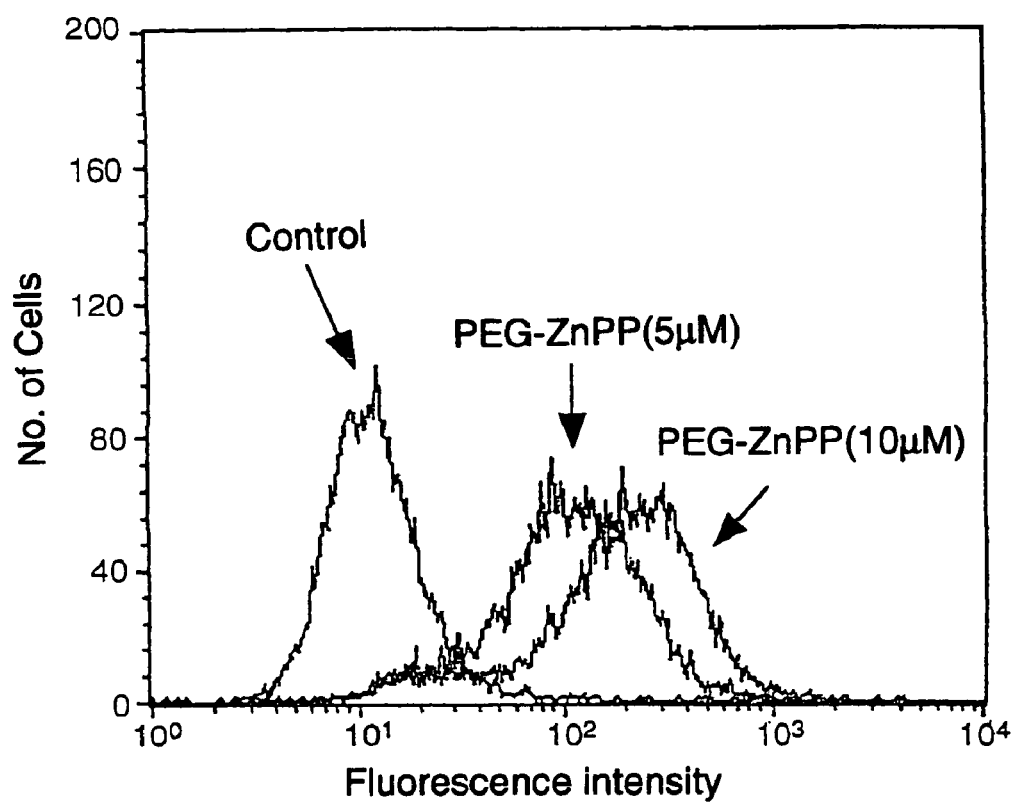
FIG. 3 shows flow-cytometric analysis data where PEG-ZnPP treated cultured cancer cells exhibiting more oxidant exposured profile.

Quantification of fluorescence intensity represents the extent of oxidative stress induced in the cells. Then, cultured cells were trypsinized and recovered cells were subjected to the flow cytometroy analysis and fluorescence cell population was quantified. The results are shown in FIG. 3, where the effect of PEG-ZnPP at 5 μM, 10 μM, is compared with that of no drug. It is clear from these data in the FIG. 3 that PEG-ZnPP brought about higher intracellular oxidative state in the dose dependent manner of PEG-ZnPP.

Experimental Example 3

Inhibition of Heme Oxygenase in Solid Tumor Model in Mouse.

In male ddY mice with mean body weight of 35 g, S 180 sarcoma cells were implanted in the dorsal skin, and when solid tumor size become 5 mm in cross diameter after about one week, PEG-ZnPP dissolved in distilled water were injected via tail vein (i.v.) at 0.5 mg ZnPP equivalent per Kg body weight. The solid tumors were removed after 24 hr, and heme oxygenase activity was quantified similarly as described in Example 1. Control mouse received distilled water without PEG-ZnPP. The tumor specimens were obtained and treated similarly. As shown in Table 1, PEG-ZnPP given i.v, (tail) showed significant reduction of the heme oxygenase activity. Unmodified ZnPP could not be administered i.v. because of its difficulty in solubility.

TABLE 1

Inhibition of intratumor heme oxygenase by PEG-ZnPP given via the tail vein.

| Drug | Activity of heme oxygenase in tumor tissue. (n mol bilirubin/ mg protein/hr) | |
| --- | --- | --- |
| Control, none | 4.17 ± 1.07 | ($P < 0.02$) |
| Group of PEG-ZnPP administered | 2.30 ± 0.54 | |
| Unmodified ZnPP administered | Impossible to solubilize in water (can not be injected) | |

Experiment 4

Antitumor Effect of PEG-ZnPP and Change of Body Weight in Mice Bearing Solid Tumor.

Figure 4:
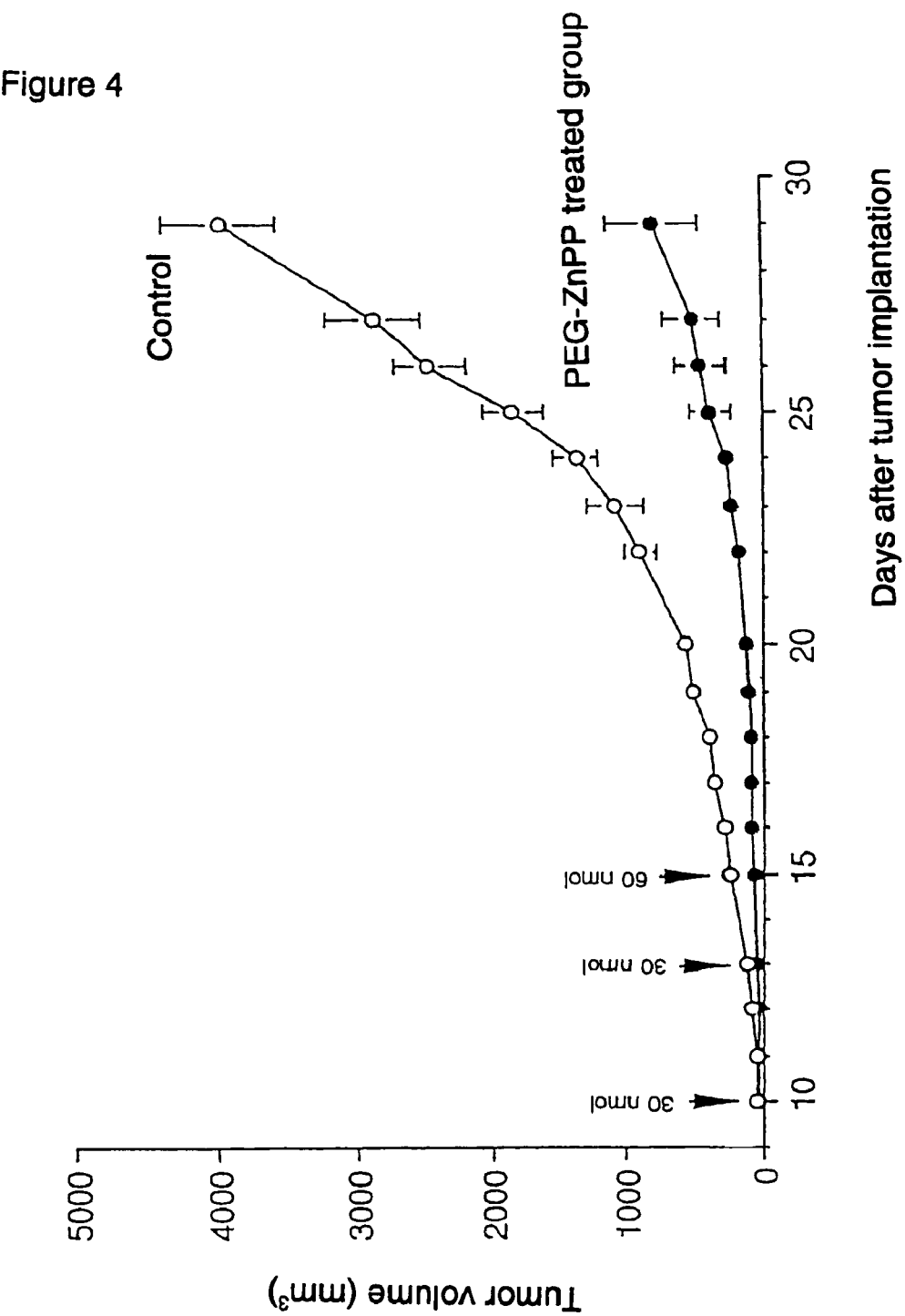
FIG. 4 shows antitumor effect of PEG-ZnPP in mouse model with solid tumor.

Similar to Experiment 3 above, sarcoma S180 of mice implanted under the dosal skin of ddY mice, and after 10, 13 and 15 days after tumor implantation, PEG-ZnPP at 30 n mole, 30 n mole and 50 n mole (3 times only), respectively, was injected into the tail vein respectively (see also arrow marks in FIG. 4). Control mice received distilled water instead of PEG-ZnPP. Sizes of tumor were measured every week day as shown in FIG. 4. It is clear that PEG-ZnPP group showed remarkable suppression of tumor growth compared with control group.

Body weight of both treated and non-treated mice were measured simultaneously as seen in FIG. 5. There was no remarkable body weight loss in the group treated with PEG-ZnPP.

Applicability of the Invention in the Industrial Sense

According to the present invention, metal porphyrin derivatives, which are inhibitory against heme oxygenase, can be made both water-soluble and lipid soluble uses and make the derivatives as intravenously injectable medicament by conjugation with amphipathic or water-soluble polymers. This is a novel medicament having excellent tumor selective accumulation. An effective preparation method of this compound was also found.

The anticancer agents according to the present invention have excellent anticancer effect without generating any appreciable side effect or toxicity.

Thus the polymer conjugated anticancer agents according to the present invention are highly useful drug having excellent tumor selective targeting property with new and different mode of action from many of the known low molecular weight anticancer drugs.

The invention claimed is:

1. A hemeoxygenase inhibitory metalloprotoporphyrin derivative which is conjugated with amphipathic or water soluble polymers represented by the general formula (A):

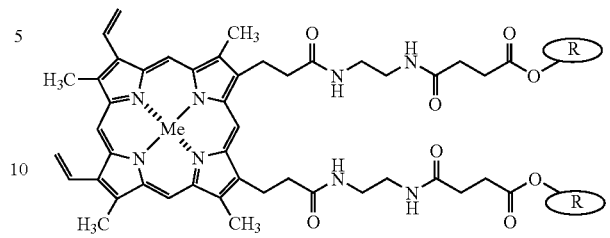

where 'R' in the above formula is an amphypathic or water soluble polymer and 'Me' is a metal.

* * * * *